United States Patent [19]

Liotta et al.

[11] Patent Number: 4,710,192
[45] Date of Patent: Dec. 1, 1987

[54] DIAPHRAGM AND METHOD FOR OCCLUSION OF THE DESCENDING THORACIC AORTA

[76] Inventors: Domingo S. Liotta; Holga E. Troncoso De Liotta, both of 3 De Febrero 2025, Buenos Aires, Argentina, 1428

[21] Appl. No.: 919,984

[22] Filed: Oct. 17, 1986

[30] Foreign Application Priority Data

Dec. 30, 1985 [AR] Argentina .............................. 302764

[51] Int. Cl.⁴ ........................ A61F 2/06; A61B 17/00; A61B 17/12
[52] U.S. Cl. ........................................ 623/1; 128/325; 128/303 R; 128/334 R; 623/11
[58] Field of Search ............... 623/1, 11, 12; 128/325, 128/303 R, 334 R, 334 C, 345

[56] References Cited

U.S. PATENT DOCUMENTS

| | | | |
|---|---|---|---|
| 3,540,431 | 11/1970 | Mobin-Uddin | 128/325 X |
| 3,874,388 | 4/1975 | King et al. | 128/334 C X |
| 4,007,743 | 2/1977 | Blake | 128/334 C X |
| 4,577,631 | 3/1986 | Kreamer | 128/325 X |

Primary Examiner—Ronald L. Frinks
Attorney, Agent, or Firm—Collard, Roe & Galgano

[57] ABSTRACT

A vaulted diaphragm for providing occlusion in a descending thoracic aorta, includes a flexible and substantially circular element, and a plurality of resilient ribs having inner and outer ends supporting the circular element. The inner ends of the ribs are joined together at a hub with the ribs extending radially outwardly therefrom. The ribs are generally positioned on and attached to the circular element with the outer ends of the ribs having protrusions projecting radially beyond the circular element. The ribs have a resilient expansion tendency, such that the diaphragm may be held in a biased folded position during installation and sprung open into a normally vaulted shape upon installation in the aorta, whereby the protrusions are urged radially outwardly by the resilient expansion tendency of the ribs to engage the aorta and hold the diaphragm in position. A surgical procedure for treating an aneurysm in a patient's descending thoracic aorta, includes the step of installing an artificial aorta by-pass connecting the patient's ascending natural aorta with the patient's abdominal aorta end. A temporary graft is installed onto the by-pass and a catheter having a capsule end holding a diaphragm is advanced through the graft. The diaphragm is positioned into a selected site in the aorta, and then released by ejecting it from the capsule and the catheter is withdrawn, with the diaphragm remaining within the aorta to provide an occlusion therein.

9 Claims, 5 Drawing Figures

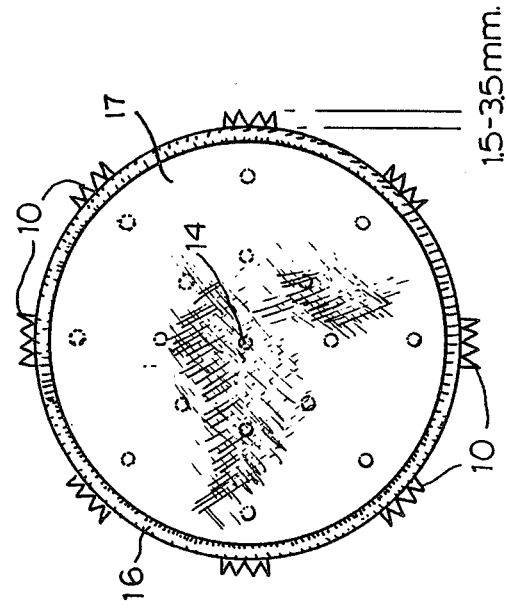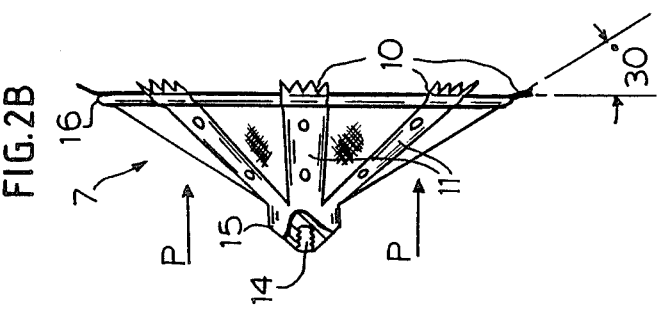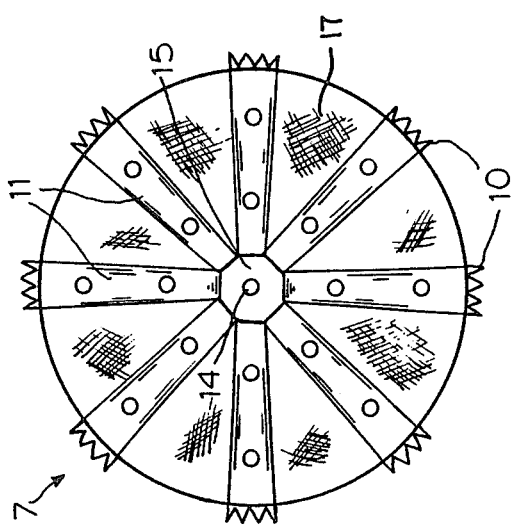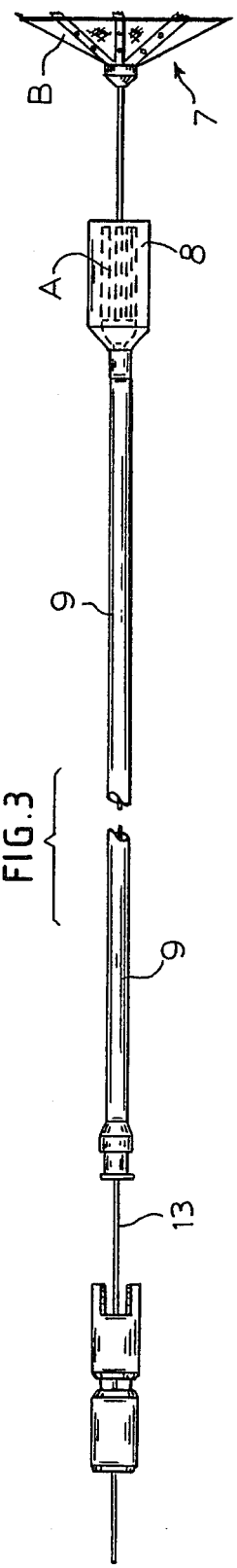

DIAPHRAGM AND METHOD FOR OCCLUSION OF THE DESCENDING THORACIC AORTA

BACKGROUND OF THE INVENTION

The invention relates to a vaulted diaphragm for occlusion of the descending thoracic aorta. More particularly, it relates to such a medical accessory diaphragm which is suitable for carrying out novel surgical techniques in the treatment of aneurysms of this artery, and is capable of being used for certain surgical operations and then remain permanently in its implantation site.

Due to the important risks involved in surgical operations for direct extirpation of descending aorta aneurysms, the use of a by-pass has been successfully employed between the ascending portion of the aorta and the abdominal portion thereof, with an anterior approach. For this purpose, a medically compatible plastic material which is located in the ventral, retrosternal position has been employed. The operation is complemented by extirpation of the aneurysm reaching the aorta through a lateral-posterior thoracotomy, commonly at a second state after the implantation of the ventral aorta.

Likewise, once the descending aorta is implanted in the ventral position, the aneurysmatical segment may be excluded from circulation, thus avoiding direct extirpation, either by means of external clamping of the diseased aorta, with a special clamp, or by direct ligature thereof.

Although the treatment of the prior art represents an advance on the usual operation of direct attack of the aneurysm, with anatomic and functional restoration by means of a plastic graft after extirpation of the aneurysm, the results are not fully satisfactory. Therefore, new processes have been developed with much more promising results due to the use of means for occluding the aorta, by internal partial or total blockage of its continuity. With the aid of fluoroscopy in the operating room, the occlusive means can be viewed in order to locate it into the correct position.

Accordingly, it is an object of the present invention to provide a vaulted diaphragm for occlusion of the descending thoracic aorta, and a method for its use.

It is also an object of the invention to provide such a diaphragm which is particularly suitable for carrying out novel surgical techniques for the treatment of aneurysms of the descending thoracic aorta.

SUMMARY OF THE INVENTION

Certain of the foregoing and related objects are readily attained with a vaulted diaphragm for providing occlusion in a descending thoracic aorta, of the type capable of isolating a portion of the aorta affected by an aneurysm. The diaphragm is installed via a surgical treatment in which a permanent arterial by-pass of medically compatible material extending from the ascending aorta to the abdominal aorta is provided. The diaphragm includes a flexible and substantially circular element, which may be a section of laminer sheet material, and a plurality of resilient ribs having inner and outer ends supporting the circular element. The inner ends of the ribs are joined together at a hub with the ribs extending radially outwardly therefrom. The ribs are generally positioned on and attached to the circular element with the outer ends of the ribs having protrusions projecting radially beyond the circular element.

The ribs have a resilient expansion tendency, such that the diaphragm may be held in a biased folded position during installation, and sprung open into its normally vaulted shape upon installation in the aorta. The protrusions are urged radially outwardly by the resilient expansion tendency of the ribs to engage the aorta and hold the diaphragm in position.

Preferably the ribs are foldable so that the diaphragm may be formed into a collapsed umbrella-like retracted assembly. The circular element preferably has a diameter of about 22 to 40 mm, and is made of a synthetic polyester fiber, such as Dacron (polyethylene terephthalate) fabric. The hub may also include a threaded hole engageable by a stylet having a threaded end, and the diaphragm may include 8 ribs. Most desirably, a cushion rim disposed around the periphery of the diaphragm is also provided.

Certain of the foregoing and related objects are also attained with a surgical procedure for treating an aneurysm in a patient's descending thoracic aorta which includes the steps of installing an artificial aorta by-pass connecting the patient's ascending natural aorta with the patient's abdominal aorta end. A temporary graft is installed onto the by-pass, and a catheter having a capsule end holding a diaphragm is advanced through the graft. The diaphragm is positioned into a selected site in the aorta, and then released by ejecting it from the capsule. Upon ejectment, the diaphragm springs open and engages the inside walls of the aorta. The catheter is withdrawn with the diaphragm remaining within the aorta to provide an occlusion therein.

Preferably the diaphragm is viewed using radioscopic or fluoroscopic means, to monitor the position of diaphragm within the patient's body. Most desirably, a stylet within the catheter is engaged onto the diaphragm to hold the diaphragm temporarily in the capsule while the catheter is advanced through the graft and while the diaphragm is moved into position within the aorta. The diaphragm is then ejected by forcing it out of the capsule by pushing on the stylet and disengaging the stylet from the diaphragm.

The vaulted diaphragm of the instant invention provides an optimum technical and scientific resource in that, in the same surgical operation, the portion of the aorta having the aneurysm is isolated, in contrast to the replacement of the aneurysmatic aorta with a synthetic graft. As a result, the operation risks are minimal and the post-operative period is very short.

The above-mentioned advantages are a direct consequence of the particular shape and construction of the occlusive diaphragm of the instant invention, which operates with a tendency towards expansion, thus maintaining its vaulted configuration, and embedding its external edge into the artery walls. This further facilitates the introduction of the diaphragm into the artery and the total occlusion thereof, so that the opening of the aorta after the occlusion is free from further blood flow entering therein.

Prior to the location of the diaphragm, a Dacron graft or by-pass similar to those mentioned, is introduced in the patient and directly connects the ascending aorta with the abdominal aorta, thus assuring the continuity of circulation. In this by-pass, a second graft, oriented towards its upper suture which connects it with the ascending aorta, is added. The second graft, which may be of smaller diameter but made of a material equivalent to that of the by-pass, forms a temporary auxiliary duct used for introducing the necessary accessories, including the diaphragm of the invention.

In order to introduce the diaphragm into the intended site, the diaphragm is collapsed or retracted, in a manner equivalent to that of a small closed umbrella, and is placed in an open-ended capsule which is carried by a guide or catheter. The diaphragm is temporarily held in place in the collapsed state within the capsule by a stylet within the catheter having a threaded end which engages a threaded hole in the center hub of the diaphragm. The catheter is then introduced into the second graft. This assembly is inserted into the interior of the aorta via the second graft, while being simultaneously viewed by fluoroscopy or similar means. When it reaches the intended position, the diaphagm is released from the capsule by pushing it out with the stylet. The diaphragm expands by means of the self resilience of its radial ribs and after it is set into position, the stylet is unscrewed from the diaphragm and the catheter may be removed. The diaphragm adopts a vaulted configuration upon release from the capsule wherein the outer ends of the ribs, are embedded with progressive force into the aortic walls where they remain fixed. The normal blood flow takes place with a direct angle of incidence on the convex face of the diaphragm, thus acting as additional load tending to embed the diaphragm. This assures that an effective occlusion is obtained and prevents the entrance of blood towards the zone affected by the aneurysm.

The closure of the aorta may also be carried out in the post-operative period, in the hemodynamics laboratory. However, the procedure might be unfeasible due to the tortuosity of subclavian arteries, as well as to the frequent obstruction of aortic bifurcation, if a femoral way is selected. The capsule carrying the diaphragm of the invention also occupies a set volume which may entirely prevent its movement through certain vessels or make its passage through diseased arteries very risky. On the other hand, a surgical procedure of great technical simplicity and safety for the patient which permits exclusion of the circulation to the descending thoracic aorta in a single surgical operation is obtained with the use of the diaphragm of the invention.

The progressive thrombosis of the aneurysmatic segment which necessarily follows the aortic occlusion attained by means of the novel diaphragm, excludes the origin of the branches derived from the descending thoracic aorta, especially those arteries irrigating the spinal cord. The irrigation of abdominal organs and lower members is assured by means of the new artificial aorta placed in the ventral position.

As previously stated, the study of the patient's aortograpy before surgery is basic in order to select the discharge and embedding (fixing) point of the diaphragm of the invention. In general, the left subclavian artery is the anatomic element serving as a guide. If the aorta is deeply dissected immediately distal to the left subclavian, it may be necessary to locate the diaphragm in the proximal aorta of the origin of this branch. In this case, the surgical process should be completed with a left carotidsubclavian by-pass. The diaphragm, as may be required for various cases, should have a diameter of about 22 to 40 mm.

With respect to the design of the diaphragm, an important factor is that the aorta may have small deformations and may not be a perfect circle, at the place selected for implanting the diaphragm. In this case, the circular flexible element of the diaphragm may expand sufficiently in order to adapt itself to the deformation basically due to the fact that each rib, individually, has sufficient resilience to open, reach and embed in the aortic wall. Once the diaphragm of the invention is located in the correct place, the guide or catheter used for positioning it is uncoupled from the diaphragm and the catheter is removed.

The diaphragm of the invention is preferably used in acute cases of ascending aortic aneurysm, where conventional surgical procedures would significantly reduce the blood flow to the upper spine from the intercostal vessels.

Other objects and features of the present invention will become apparent from the following detailed description when taken in connection with the accompanying drawings which disclose one embodiment of the invention. It is to be understood that the drawings are designed for the purpose of illustration only, and are not intended as a definition of the limits of the invention.

BRIEF DESCRIPTION OF THE DRAWINGS

In the drawings, wherein similar reference characters denote similar elements throughout the several views:

FIG. 2A is a top plan view of the diaphragm in the extended or open position;

FIG. 2B is a side elevational view thereof;

FIG. 2C is a bottom elevational view thereof; and

FIG. 3 is a fragmentarily illustrated front elevational view of the catheter used to surgically implant the diaphragm of the invention.

DETAILED DESCRIPTION OF THE PREFFERED EMBODIMENT

Figure 1:
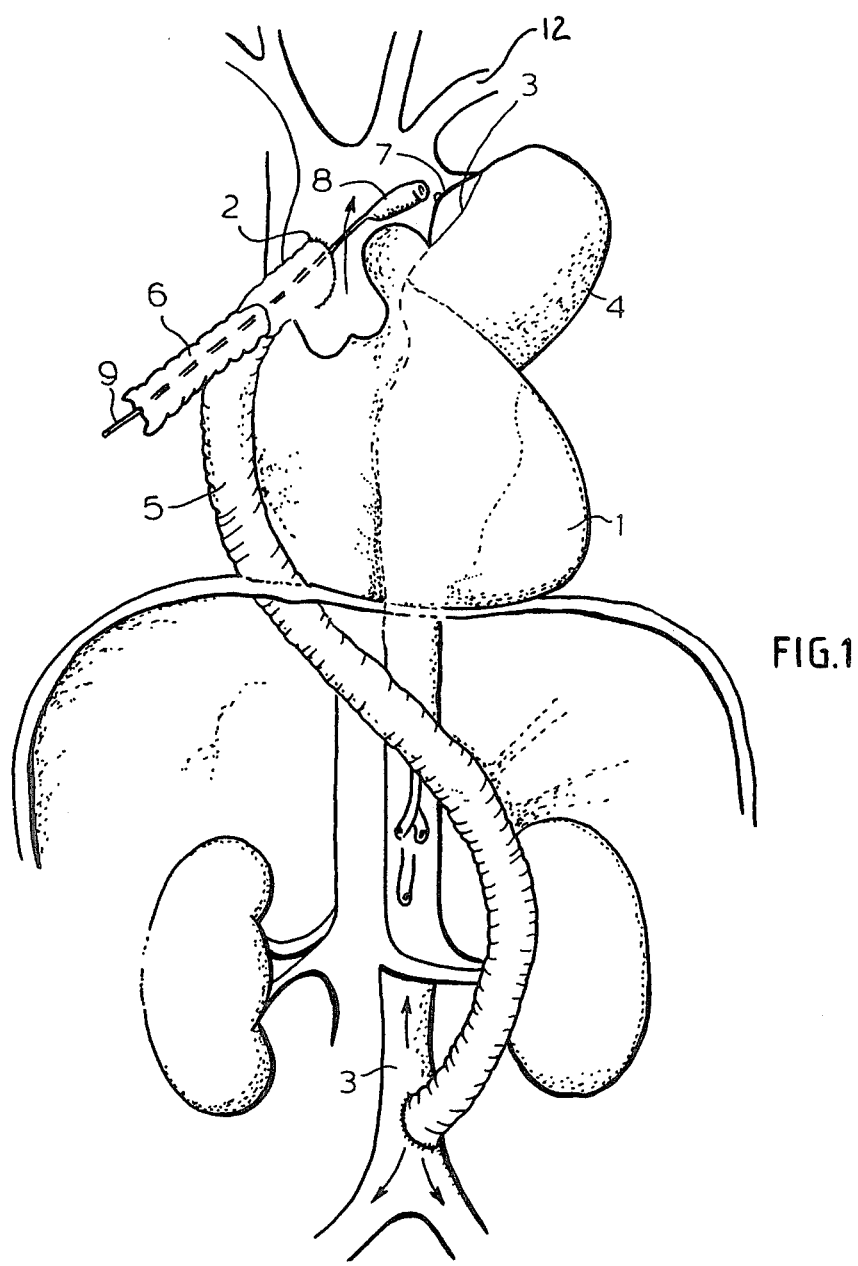
FIG. 1 is a fragmentarily-illustrated schematical front view of the thoracic and abdominal regions showing some organs, an artificial aorta having a transitory branch sutured thereto, and a catheter for locating the diaphragm of the invention to occlude a bulky aneurysm developed in the descending portion of the aorta.

Turning now in detail to the appended drawings, as shown in FIG. 1, the ascending aorta 2 starts at the heart 1 and posteriorly extends following the descending thoracic aorta 3 which leads to the abdominal aorta in which it bifurcates forming the two iliac arteries. In the region of descending thoracic aorta 3, there is a bulky aneurysm 4, i.e., the patient's diseased condition. Aneurysm 4 is treated by means of the use of the diaphragm 7 via an operation technique especially developed for this purpose.

In the performance of the operation, a by-pass or artificial aorta 5 made of Dacron or any compatible material is initially introduced into the patient. By-pass 5 which will be permanently incorporated into the patient, connects the ascending natural aorta 2 with the abdominal end thereof. A temporary graft 6 is added to by-pass 5, for the purposes of the surgical operation, at a location close to the region of the suture with ascending aorta 2. A catheter 9 is then inserted into temporary graft 6. In a capsule 8 at the end of catheter 9, diaphragm 7 is temporarily held in place in position "A", as shown in phantom in FIG. 3, in a folded or collapsed condition similar to that of a small umbrella. A stylet 13 within catheter 9 having a threaded end engages a threaded hole 14 in the center hub of diaphragm 7, and securely holds diaphragm 7 into capsule 8 until diaphragm 7 is properly positioned. With the aid of simultaneous radioscope viewing, or the like, the folded diaphragm is maneuvered to the proper previously selected site, and is ejected from capsule 8 by pushing on stylet 13, with the diaphragm placed into position "B" as illustrated in FIG. 3. Upon ejection, the protruding ends 10 of radial ribs 11 of diaphragm 7 expand out and are embedded or fixed into the aortic wall. The position of the diaphragm in the aortic wall is then confirmed using fluoroscopy, or even with an aortography, if necessary. Stylet 13 is then unscrewed from diaphragm 7 and is withdrawn with catheter 9.

As shown in FIG. 2B, blood pressure in the direction of arrows P aids this embedment in order to more securely fix the occlusive diaphragm. The left subclavian 12, as shown in FIG. 1, is often taken as a guide element to select the proper place for locating diaphragm 7. Also shown in FIG. 1 are some branches of the descending aorta which constitute arteries irrigating the spinal cord or other organs, the details of which do not affect the novel aspects of the diaphragm of the invention. However, these arteries may continue their function by means of the blood flow from by-pass 5 through the descending aorta and upwardly from its lower part.

As shown best in FIG. 2A, diaphragm 7 includes a plurality of ribs 11, e.g. 8 ribs, radially attached to a center diaphragm hub 15. Ribs 11 and hub 15 may be made of Elgiloy, a metal alloy made by American Edwards Laboratories of Santa Ana, Calif., a metal alloy having a high spring coefficient. Ribs 11 can be attached to hub 15 by resistance welding, to form an umbrella-like frame structure. This structure is covered on both sides with e.g., medical grade Dacron fabric to form a flexible and generally circular laminar element 17. Around the outside perimeter of the diaphragm is a rim cushion 16, also made of e.g., Dacron cloth. Upon installation of the diaphragm, rim 16 is urged radially outwardly by the spring force of ribs 11 and contacts the endothelium or inside walls of the e.g., thoracic aorta. At the ends of ribs 11 are protrusions or points 10 which extend from 1.5-3.5 mm beyond rim 16 for engaging the vessel wall to secure the diaphragm in place. The diameter of the rim typically is 22, 34, or 36 mm. When diaphragm 7 is in the open or installed position, ribs 11 form an angle of about 30° with the plane of rim cushion 16.

Thus, while only a single embodiment of the present invention has been shown and described, it will be obvious that many changes and modifications may be made thereunto, without departing from the spirit and scope of the invention.

What is claimed is:

1. A diaphragm for providing occlusion in a descending thoracic aorta, of the type capable of isolating a portion of the aorta affected by an aneurysm, and installed via a surgical treatment in which a permanent arterial by-pass of medically compatible material extending from the ascending aorta to the abdominal aorta is provided, said diaphragm comprising:
    a flexible and substantially circular element, said circular element including a cushion rim around the outer periphery thereof, said cushion rim having a thickness substantially greater than said circular element; and
    a plurality of resilient ribs having inner and outer ends supporting said circular element, said inner ends of said ribs joined together at a hub with said ribs extending radially outwardly therefrom, said ribs generally positioned on and attached to said circular element with said outer ends of said ribs having protrusions projecting radially beyond said cushion of said circular element, said ribs having a resilient expansion tendency, such that said diaphragm may be held in a biased collapsed position during installation, and sprung open into a normally vaulted shaped upon installation in the aorta, whereby said protrusions are urged radially outwardly by the resilient expansion tendency of said ribs to engage the aorta and hold said diaphragm in position.

2. The diaphragm of claim 1, wherein said ribs are spring-like so that said diaphragm may be collapsed into a retracted umbrella-like assembly.

3. The diaphragm of claim 1, wherein said circular element has a diameter of about 22 to 40 mm.

4. The diaphragm of claim 1, wherein said hub includes a threaded hole engageable by a stylet having a threaded end.

5. The diaphragm of claim 1, wherein said diaphragm includes 8 ribs.

6. The diaphragm of claim 1, wherein said flexible and substantially circular element is made of polyethylene terephthalate fabric.

7. A surgical procedure for treating an aneurysm in a patient's descending thoracic aorta, comprising the steps of:
    installing an artificial aorta by-pass connecting the patient's ascending natural aorta with the patient's abdominal aorta end;
    installing a temporary graft onto said by-pass; and
    advancing a catheter having a capsule end holding a retracted diaphragm through said graft;
    positioning said diaphragm into a selected site in said aorta; and
    releasing the diaphragm by ejecting it from the capsule thereby allowing said diaphragm to spring open into a vaulted shape and engage the inner walls of aorta all around; and
    withdrawing the catheter with the diaphragm remaining within the aorta to provide an occlusion therein.

8. The procedure of claim 7, further comprising the step of viewing the diaphragm using radioscopic or fluoroscopic means, to monitor the position of diaphragm within the patient's body.

9. The procedure of claim 7, further comprising the steps of:
    engaging a stylet within the catheter onto the diaphragm to hold the diaphragm temporarily in the capsule while the catheter is advanced through the graft and while the diaphragm is moved into position within the aorta; and
    ejecting the diaphragm by forcing it out of the capsule by pushing on the stylet and disengaging the stylet from the diaphragm.

* * * * *